United States Patent [19]

McRae

[11] Plant 4,180

[45] Jan. 3, 1978

[54] LILY PLANT: LILIUM 'CHARISMA'

[75] Inventor: Edward A. McRae, Boring, Oreg.

[73] Assignee: Melridge, Inc., Gresham, Oreg.

[21] Appl. No.: 761,232

[22] Filed: Jan. 21, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant bearing large clusters of medium-sized flowers of excellent form, strong color, and long persistence, both on the plant and as a cut flower; the flowers of the new plant are characterized particularly by their unique vibrant golden-orange color and by the distinctive pattern of the color tones on the tepals. The flowers are completely unspotted. The plant is highly resistant to disease and shows high tolerance to virus. It is an excellent garden plant. The bulbs may be precooled and forced as pot plants, retaining their short stature without chemical treatment. The clone is very vigorous and is an excellent grower and propagator.

1 Drawing Figure

BACKGROUND OF THE INVENTION

My new variety of lily plant originated as a seedling selected from a group of seedlings at Gresham, Oreg. The seedlings were planted as a result of breeding efforts carried on by me since the year 1968. The breeding efforts had as their objective the production of upright flowering Asiatic lilies with miniature bushy plants suitable without chemical dwarfingfor pot culture, mass planting, and landscape work.

I achieved the desired objective by using as a seed parent Lilium 'Cinnabar' and as the pollen parent Lilium 'Red Carpet'.

My new lily plant is characterized by a miniature bushy plant habit well suited for pot culture, mass planting, and landscape work. The leaves are exceptionally long for any lily.

The flower color is exceptional; the tepals have golden-orange midribs shading into brilliant orange along the tepal margins.This grading of color is produced within all tissues of the tepal and represents a new color pattern; in other lilies with deeper colored margins, the deeper pigment is carried only in the epidermis of the tepals. This flower color, in an unspotted flower, is a totally new combination in Asiatic hybrid lilies. The unusally dark pollen emphasizes the color of the flower.

The plant is an exceptional grower and is highly tolerant to virus and resistant to the diseases that usually plague lilies and impair their forcing performance.

The clone has given excellent performance in forcing trials in which the bulbs are precooled and forced out of season. Its uniformity of forcing is remarkable even for a clone. The plant will flower in from 60 to 65 days, a characteristic of tremendous commercial importance. Several blooms of medium size are produced on a single stalk; the majority of 6 to 7 inch in circumference bulbs will produce plants with two stems, with an average total of 5 to 8 buds.

My new variety of lily plant has been asexually reproduced by me and under my direction at Gresham, Oreg. Successive generations produced by bulb scale propagation and natural multiplication from bulblets have demonstrated that the novel and distinctive characteristics of my new variety are fixed and hold true from generation to generation.

DESCRIPTION OF THE DRAWING

My new variety of lily plant is illustrated in the accompanying photographic drawing which shows the bud and the open blooms in full color and illustrates the flower form, the tepal arrangement, the connection of the flowers to the stalk, the vibrant, pure, orange-yellow color of the flower, and the long-leaved, bushy character of the plant.

DESCRIPTION OF THE NEW VARIETY

The following is a detailed description of my new variety of Asiatic hybrid lily, with nomenclature according to *The International Lily Register,* (Royal Horticultural Society, London, 2nd Edition, 1969), and with color designations according to the Royal Horticultural Society Color Chart published by the R.H.S. in 1966.

THE PLANT

Origin: Seedling.

Parentage:

*Seed parent.*—Lilium 'Cinnabar'.

*Pollen parent.*—Lilium 'Red Carpet'.

Classification:

*Botanic.*—Lilium hybrid clone; Division I-A of Horticultural Classification of Lilies, R.H.S.

*Commercial.*—Asiatic hybrid lily.

Form: Single stem, erect and bushy.

Height: 15 inches.

Growth: Very vigorous, upright and sturdy.

Foliage:

*Quantity.*—Abundant.

*Size of leaf.*—6 to 8 inches long.

*Shape of leaf.*—Lanceolate.

*Texture.*—Leathery and glossy.

*Color.*—Upper and under sides, both bottle green.

Bulbs:

*Size.*—Any size, ranging to 12 inches in circumference.

*Color.*—Pure white.

THE BUD

Form: Obtuse, urn-shaped and long.

Size: 2½ to 3 inches long and 1½ inches in diameter at maturity.

Opening: Bud opens slowly.
Color: Golden-orange (vibrant orange) when tepals first divide and also when tepals begin to unfurl.
Tepals: Curl back.
Color: Golden-orange with brilliant orange margins on the inside and golden-orange on the outside.
Peduncle: 2 inches long, erect, and soft green in color.

THE FLOWER

Blooming habit: Annually in early summer. Blooms once and profusely.
Size: Medium; about 5 to 6 inches in diameter.
Borne: In clusters, 3 to 8 per stem. A bulb 6 to 7 inches in circumference usually produces two stems, each with 2 to 4 flowers.
Shape: Cup-shaped. Tepals recurve as bloom matures.
Tepalage:
*Number of tepals.*—6.
*Arrangement.*—Imbricated.
*Color.*—Yellow orange R.H.S. C.C.24A at midrib and R.H.S. C.C.32A on remaining areas of tepals.
*Tepal longevity.*—Tepals stay on stem about 3 weeks.
Pedicel:
*Length.*—2 inches.
*Color.*—Soft green.
*Form.*—Pedicel is sturdy and upright.
Color Permanence: Flowers do not fade.
Appearance: The flower is shiny.
Disease resistance: The plants are resistant to disease; in particular, they are resistant to Fusarium and Botrytis.
Fragrance: The flower is not fragrant.

Lasting quality: The flower is long lasting both on the plant and as a cut flower.

THE REPRODUCTIVE ORGANS

Stamens, anthers:
*Arrangement.*—Typical of Liliaceae.
*Length.*—2 inches.
*Number.*—6.
Pollen: Dark red-brown in color.
Pistils: One in number with a length of about 2 inches.
Stigmas: Light green in color.
Characteristics of ovaries: Typical of genus Lilium.

THE FRUIT

Fertility: The fruit is fertile.
Shape: The fruit is ovoid.
Color at maturity: The fruit is soft brown.

My new variety of Asiatic hybrid lily is unique in its class. It does not resemble any other lily known and in commercial production at the present time.

I claim:

1. A new and distinctive variety of Asiatic hybrid lily plant substantially as herein shown and described, characterized by the distinctive genetically short habit of the plant, the exceptional length of the plant leaves, the resistance of the plant to disease; its high tolerance of viral infection; the vigorous growth and propagation characteristics of its clone; the excellence of its flower form; the versatility of the plant both as a garden plant and as a pot plant uniformly and rapidly forced out of season from precooled bulbs; and in particular by the pure, unspotted, vibrant golden-orange color of its flowers.

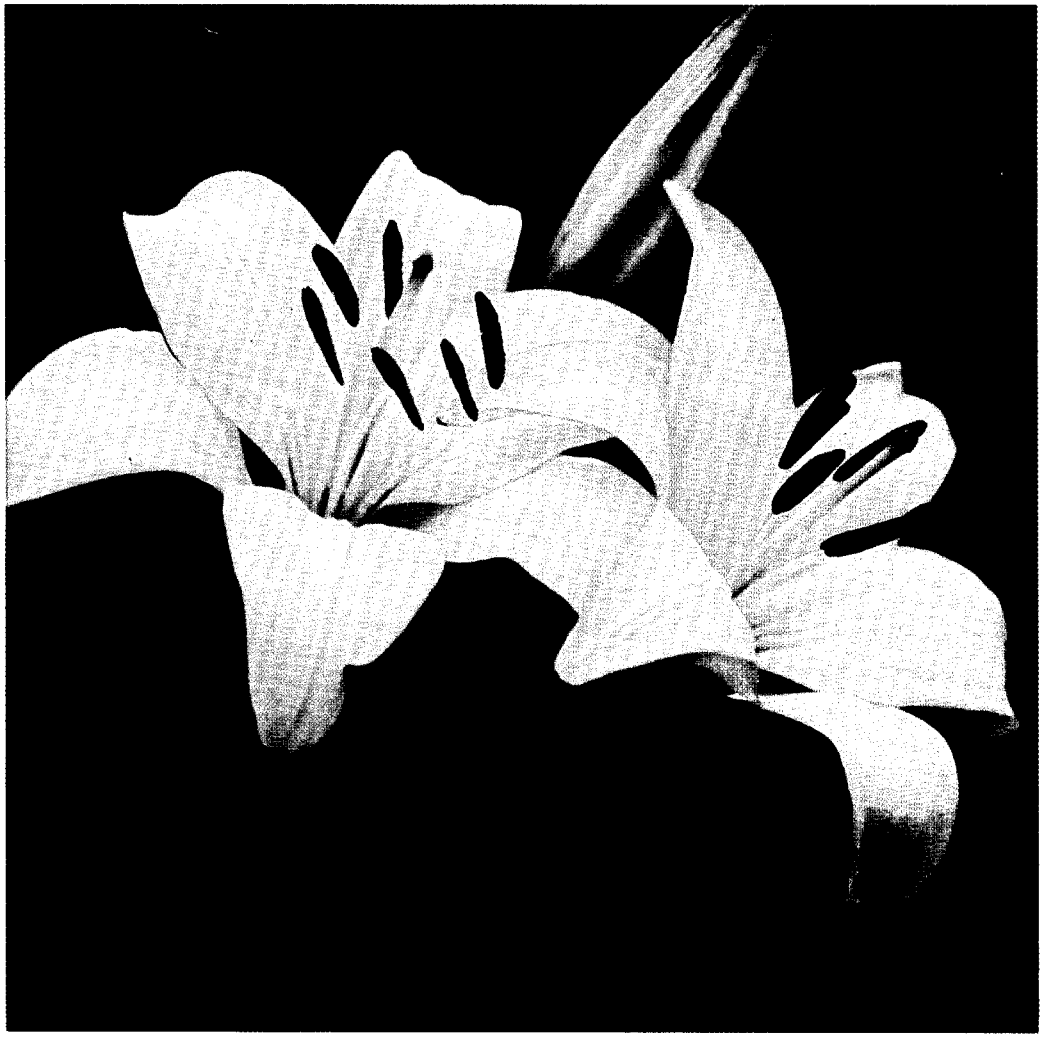

* * * * *